US009329155B2

(12) United States Patent
Goldammer et al.

(10) Patent No.: US 9,329,155 B2
(45) Date of Patent: May 3, 2016

(54) METHOD AND DEVICE FOR DETERMINING AN ORIENTATION OF A DEFECT PRESENT WITHIN A MECHANICAL COMPONENT

(71) Applicant: SIEMENS AKTIENGESELLSCHAFT, München (DE)

(72) Inventors: Matthias Goldammer, München (DE); Werner Heinrich, Oberkrämer OT Bärenklau (DE); Hubert Mooshofer, München (DE)

(73) Assignee: SIEMENS AKTIENGESELLSCHAFT, München (DE)

( * ) Notice: Subject to any disclaimer, the term of this patent is extended or adjusted under 35 U.S.C. 154(b) by 0 days.

(21) Appl. No.: 14/803,388

(22) Filed: Jul. 20, 2015

(65) Prior Publication Data

US 2015/0323506 A1 Nov. 12, 2015

Related U.S. Application Data

(63) Continuation of application No. 13/822,405, filed as application No. PCT/EP2011/065269 on Sep. 5, 2011, now abandoned.

(30) Foreign Application Priority Data

Sep. 16, 2010 (DE) ......................... 10 2010 040 856

(51) Int. Cl.
*G01N 29/44* (2006.01)
*G01N 29/04* (2006.01)
*G01N 29/06* (2006.01)

(52) U.S. Cl.
CPC ............ *G01N 29/4445* (2013.01); *G01N 29/04* (2013.01); *G01N 29/043* (2013.01); *G01N 29/069* (2013.01); *G01N 2291/044* (2013.01)

(58) Field of Classification Search
CPC .............. G01N 29/4445; G01N 29/04; G01N 2291/044; G01N 29/043; G01N 29/069
USPC ............................................................ 73/602
See application file for complete search history.

(56) References Cited

U.S. PATENT DOCUMENTS 4,457,176 A * 7/1984 Scholz .................. G01N 29/11 73/624
4,991,427 A * 2/1991 Nottingham ............ G01S 15/88 73/623
6,487,909 B2 * 12/2002 Harrold ................ G01N 29/228 73/593

(Continued)

*Primary Examiner* — J M Saint Surin

(57) ABSTRACT

A technique is provided for determining an orientation of a defect present within a mechanical component using at least one ultrasonic head that applies ultrasonic signals to the mechanical component starting from various measurement points. Echo ultrasonic signals reflected by a point to be analyzed present within the component back to the measurement points are received by the same or a different ultrasonic head. A data processing unit analyzes the received echo ultrasonic signals as a function of a sound emission direction between each measurement ping and the point to be analyzed for determining the orientation of the defect. A distance between the measurement point and the point to be analyzed is calculated for every measurement point as a function of a signal propagation time between the point in time of emitting the ultrasonic signal and the point in time of receiving the echo ultrasonic signal reflected by a defect.

22 Claims, 2 Drawing Sheets

(56) References Cited

U.S. PATENT DOCUMENTS 8,038,895 B2 * 10/2011 Koester ................ G01N 29/043 117/14
8,656,782 B2 * 2/2014 Boehm ................ G01N 29/069 73/602
2013/0192381 A1 * 8/2013 Becker .................... B29C 73/10 73/802

* cited by examiner

METHOD AND DEVICE FOR DETERMINING AN ORIENTATION OF A DEFECT PRESENT WITHIN A MECHANICAL COMPONENT

CROSS REFERENCE TO RELATED APPLICATIONS

This application is a continuation of application Ser. No. 13/822,405 of the US National Stage of International Application No. PCT/EP2011/065269, filed Sep. 5, 2011 and claims the benefit thereof. The International Application claims the benefits of German application No. 102010040856.5 DE filed Sep. 16, 2010. All of the applications are incorporated by reference herein in their entirety.

FIELD OF INVENTION

The invention relates to a method and a device for determining an orientation of a defect present within a mechanical component by means of ultrasonic examination.

BACKGROUND OF INVENTION

Ultrasonic examination is a non-destructive material testing procedure for investigating components made from sound-conducting materials such as metal, plastics, ceramic material or concrete, for internal and external faults and defects and inhomogeneities of all types, in particular, cracks, slag inclusions, cavities, etc.

As a result of the simple and universal applicability coupled with the fact that test personnel are not exposed to any radiation burden, ultrasonic examination methods are one of the most commonly used non-destructive material testing methods.

Using ultrasonic testing methods, for example, large forged parts such as wheel disks, shafts or hollow shafts which are subject to large loads in operation are tested with ultrasound, possibly after manufacturing and possibly in a relatively uncontoured state. If defects are found with the ultrasonic testing method, a decision can be made, based on the defect discovered, whether the tested component will be put to use or not.

For the recognition and better characterization of defects, the SAFT method (Synthetic Aperture Focusing Technique) is sometimes used. With in-phase addition of the measured ultrasonic signals, for each point in the volume of the component to be examined, a localized defect indication is obtained. In a variant of the SAFT method, the FT-SAFT method, signal analysis is carried out for faster calculation in the frequency range.

However, a disadvantage of the conventional SAFT method lies therein that no information is thereby obtained concerning the orientation or alignment of relatively small defects within the component, which can be significant for the assessment of whether a component will be used. The orientation of an existing defect can have varying significance depending on the specific loading and geometry of an individual component. If the component is, for example, a wheel disk, radially oriented defects within the component are problematic since tangential tensional forces promote the growth of the defect or crack. Tangentially oriented defects or cracks, on the other hand, can be more readily tolerated in the component.

SUMMARY OF INVENTION

It is therefore an object of the present invention to provide a method and a device for determining an orientation of a defect present within a mechanical component.

This object is achieved according to the features of the independent claim(s).

The invention provides a method for determining an orientation of a defect present within a mechanical component, comprising the steps:

a) applying ultrasonic signals emitted from various measuring points to the mechanical component, wherein the ultrasonic signals are generated by at least one ultrasonic head which applies an ultrasonic signal to the component from each of the measuring points, wherein an echo ultrasonic signal thereby generated is received temporally offset by the same ultrasonic head or a different ultrasonic head in each case;

b) analyzing the received echo ultrasonic signals which are reflected from a point to be investigated within the component back to the measuring points, depending on an application direction between the respective measuring point and the point under investigation of the component in order to determine the orientation of a defect;

c) wherein, depending on a detected signal propagation time between the time point of emission of the ultrasonic signal and the time point of reception of the reflected echo ultrasonic signal for each measuring point, a distance between the measuring point and the point to be investigated is calculated and the echo ultrasonic signals from the point to be investigated and received temporally offset at the different measuring points are added together in phase for the analysis thereof.

In one embodiment of the method according to the invention, the echo ultrasonic signals received temporally offset at the different measuring points are added together in phase taking account of an angular characteristic of the ultrasonic head.

In another possible embodiment of the method according to the invention, in order to determine the orientation of the defect, a mean value or a median value is calculated.

In another embodiment of the method according to the invention, a measure for the directional effect of the defect, in particular a standard deviation, is calculated.

In another possible embodiment of the method according to the invention, the different echo ultrasonic signals that are received at the different measuring points by the ultrasonic head are placed in intermediate storage in a memory store together with the spatial coordinates of the respective measuring point for analysis.

In a preferred embodiment of the method according to the invention, an envelope curve is determined for the echo ultrasonic signals placed in intermediate storage.

In another possible embodiment of the method according to the invention, for this purpose, the echo ultrasonic signals placed in intermediate storage are rectified and low-pass filtered.

In another alternative embodiment of the method according to the invention, the echo ultrasonic signals placed in intermediate storage are subjected to a Hilbert transformation and absolute value generation.

In another possible embodiment of the method according to the invention, an angular characteristic of the rectified echo ultrasonic signals is statistically analyzed depending on the sound emission direction.

In another possible embodiment of the method according to the invention, analysis of the echo ultrasonic signals received takes place only once the signal amplitude of the in-phase added-together echo ultrasonic signals exceeds a settable threshold value.

In another possible embodiment of the method according to the invention, a direction-dependent in-phase addition of the echo ultrasonic signals is carried out, in particular by weighting with a sine factor or a cosine factor.

In another possible embodiment of the method according to the invention, a two-dimensional plane orientation angle is output as the orientation of the defect.

In another alternative embodiment of the method according to the invention, a three-dimensional solid orientation angle of the defect is output as the orientation of the defect.

In another possible embodiment of the method according to the invention, depending on the determined orientation of the defect present in the component and based on stored geometric data concerning the component, a future failure probability of the component is calculated.

In another possible embodiment of the method according to the invention, in order to calculate the failure probability of the component, mechanical loading forces which act upon the component during operation are taken into account.

In another possible embodiment of the method according to the invention, during an analysis of an indication, the orientation as determined is taken into account in order to detect a correct indication variable.

The invention also provides a device for determining an orientation of a defect present within a mechanical component, comprising:

- at least one ultrasonic head which applies ultrasonic signals to the mechanical component from various measuring points, wherein echo ultrasonic signals which are reflected by a point to be investigated present within the component to the measuring points, are received by the same or another ultrasonic head; and
- a data processing unit which analyzes the received echo ultrasonic signals depending on a sound emission direction between the respective measuring point and the point to be investigated for determining the orientation of the defect, wherein, depending on a detected signal propagation time between the time point of emission of the ultrasonic signal and the time point of reception of the echo ultrasonic signal reflected by a defect for each measuring point, a distance between the measuring point and the point to be investigated is calculated and the echo ultrasonic signals of the point to be investigated received temporally offset at the various measuring points are added together in phase for the analysis thereof.

In another possible embodiment of the device according to the invention, the ultrasonic signals are generated by at least one ultrasonic head which is movably arranged on the surface of the mechanical component and applies ultrasonic signals to the mechanical component from the measuring points.

In another possible embodiment of the device according to the invention, the ultrasonic signals are generated by an array test head with a plurality of ultrasonic heads.

In another possible embodiment of the device according to the invention, said device has a memory store which places the various echo ultrasonic signals that are received at the different measuring points together with the spatial coordinates of each measuring point into intermediate storage for further analysis.

In another possible embodiment of the device according to the invention, the echo ultrasonic signals placed into intermediate storage are subjected to a Hilbert transformation by a transforming unit and to absolute value formation.

In another alternative embodiment of the device according to the invention, the echo ultrasonic signals placed into intermediate storage in the memory store are rectified by a transforming unit and low-pass filtered.

In another possible embodiment of the device according to the invention, said device comprises an analyzing unit which statistically analyzes an angular characteristic which gives the dependency of the signal amplitude on a sound emission direction.

In another possible embodiment of the device according to the invention, the analyzing unit calculates a future failure probability for the component based on the orientation of the defect present in the component as determined and based on stored geometric data of the component.

The invention also provides a machine and a device for determining an orientation of a defect present within a mechanical component, comprising:

- at least one ultrasonic head which applies ultrasonic signals to the mechanical component from various measuring points, wherein echo ultrasonic signals which are reflected by a point to be investigated present within the component to the measuring points, are received by the same or another ultrasonic head; and
- a data processing unit which analyzes the received echo ultrasonic signals depending on a sound emission direction between the respective measuring point and the point to be investigated, in order to determine the orientation of the defect, wherein, depending on a detected signal propagation time between the time point of emission of the ultrasonic signal and the time point of reception of the echo ultrasonic signal reflected by a defect for each measuring point, a distance between the measuring point and the point to be investigated is calculated and the echo ultrasonic signals of the point to be investigated received temporally offset at the various measuring points are added together in phase for the analysis thereof, wherein the device monitors components of the machine to determine an orientation of a defect occurring within the component.

BRIEF DESCRIPTION OF THE DRAWINGS

Possible embodiments of the device according to the invention and the method according to the invention for determining an orientation of a defect present within a mechanical component will now be described making reference to the attached figures, in which.

DETAILED DESCRIPTION OF INVENTION

Figure 1:
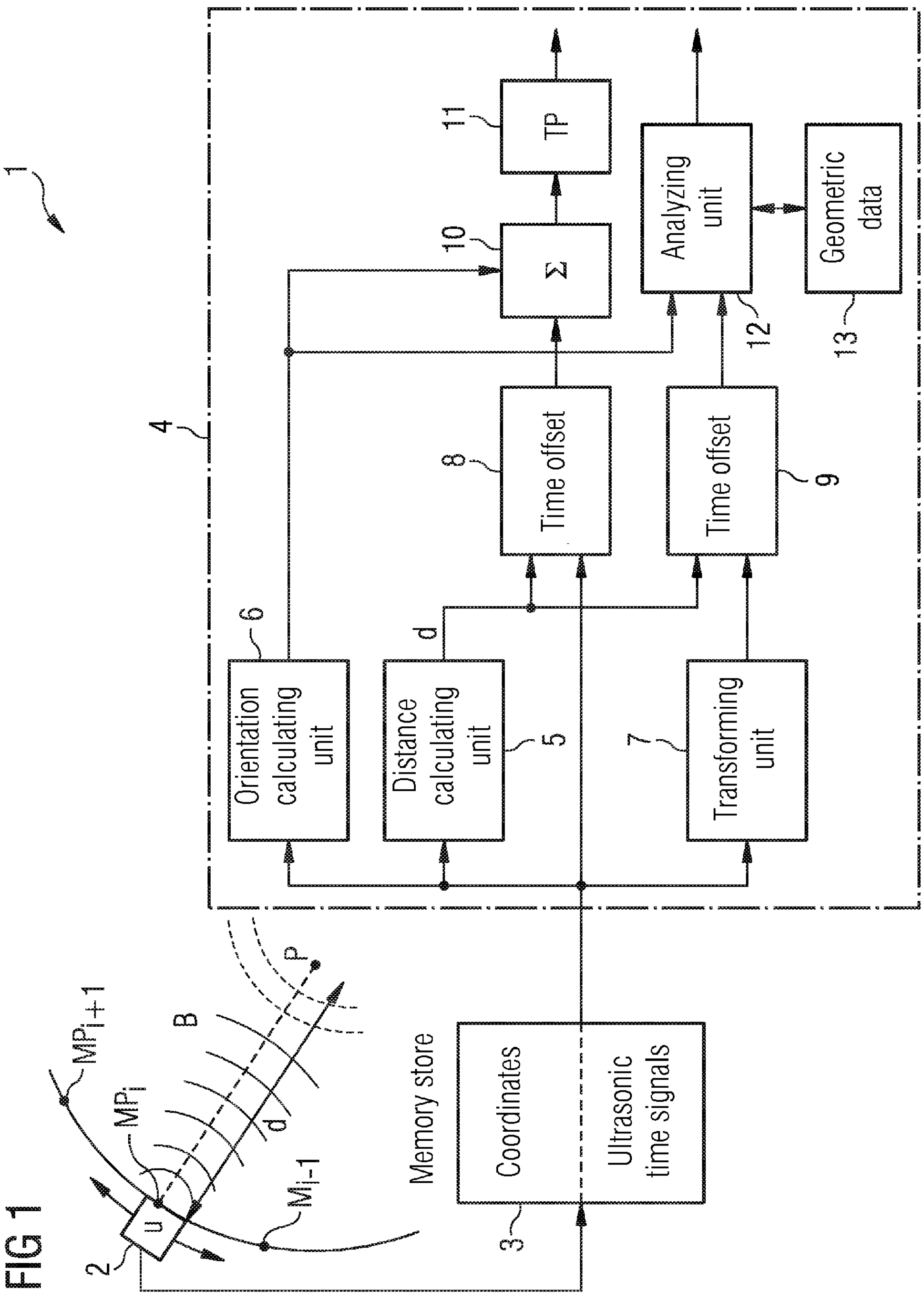
FIG. 1 is a block circuit diagram of a possible embodiment of the device according to the invention for determining an orientation of a defect present within a mechanical component.

As FIG. 1 shows, the device 1 according to the invention for determining an orientation of a defect present within a mechanical component B comprises at least one ultrasonic head 2 which applies ultrasonic signals to the mechanical component from various measuring points MP. Echo ultrasonic signals which are reflected by a point P to be investigated present within the component B to the measuring points MP, are received by the same or another ultrasonic head.

In another possible embodiment, the ultrasonic signals are generated by an ultrasonic head 2 which is movably arranged on the surface of the mechanical component B and applies ultrasonic signals to the mechanical component B from the various measuring points MP.

In a possible embodiment, the ultrasonic signals are generated by an array test head having a plurality of ultrasonic heads 2.

The sound propagation within the component takes place in the form of an elastic wave which is bound to the material of the component B. The material can be a solid, liquid or gaseous substance. No material is transported during the sound propagation, rather the material particles of the component B which consists, for example, of atoms, ions or molecules of the respective propagating medium, oscillate periodically at the locations thereof about a rest position and thereby transfer the movement thereof to adjacent particles. In this way, the oscillation process propagates at a sound velocity that is characteristic for the propagation medium or component material. Sound at a frequency of above 20 kHz is generally known as ultrasound. The generation of ultrasound by the ultrasonic head 2 can be performed in a variety of ways. For example, a piezoelectric effect or a magnetostrictive effect can be utilized. In one possible embodiment, the ultrasonic head 2 serves, as shown in FIG. 1, both as a transmitter and a receiver of ultrasonic waves. Alternatively, the echo ultrasonic signal reflected by the point P to be investigated can be received by another ultrasonic head. Ultrasonic waves propagate in straight lines. If, however, ultrasonic waves meet border surfaces during the passage thereof through the test object or component B, for example, border surfaces caused by pores, cavities, cracks or slag inclusions, the ultrasonic signals do not pass beyond such fault sites, but are reflected thereby. During the ultrasonic examination, either the transmitted or the reflected sound portions can be measured. Reflection, or echo, ultrasonic methods have different advantages, and in particular, the position in depth of a defect or error can be determined. Furthermore, in the case of the echo ultrasonic method, the component under investigation need only be accessible from one side.

Furthermore, no precise orientation between the transmitter and the receiver are required because only one coupling surface is present for the ultrasonic head 2.

As FIG. 1 shows, the various echo ultrasonic signals which are received at the different measuring points MP are placed into intermediate storage in a data store 3 for further analysis. The data store 3 therefore contains the coordinates of each of the measuring points $MP_i$ and the associated sampled echo ultrasonic signals of each measuring point MP. The device 1 also has a data processing unit 4 which analyzes the echo ultrasonic signals for the various measuring points $MP_i$ placed into intermediate storage in the data store 3. The data processing unit 4 analyzes the received echo ultrasonic signals depending on a sound emission direction between the respective measuring point $MP_i$ and the point P to be investigated in order to determine the orientation of a defect. Depending on a detected signal propagation time between the time point of emission of the ultrasonic signal and the time point of reception of the reflected echo ultrasonic signal reflected by a defect for each measuring point $MP_i$, a distance d between the measuring point $MP_i$ and the point P to be investigated is calculated and the echo ultrasonic signals from the point P to be investigated and received temporally offset at the different measuring points $MP_i$ are added together in phase for the analysis thereof.

In the exemplary embodiment shown in FIG. 1, the data processing unit 4 has a distance calculating unit 5 which calculates a distance d between the respective measuring point MP and the point P to be investigated. The data processing unit 4 also comprises a direction calculating or orientation calculating unit 6 which analyzes the received echo ultrasonic signals which are reflected by the point P present within the component B and under investigation, to the measuring point $MP_i$, depending on a sound emission direction between the respective measuring point MP and the point P of the component B to be investigated, in order to determine the orientation of the defect.

The data processing unit 4 also comprises an optional signal transforming unit 7. Said transforming unit 7 calculates an envelope curve for each of the echo ultrasonic signals placed in intermediate storage. In one possible embodiment, the echo ultrasonic signals placed into intermediate storage are rectified and low-pass filtered by the transforming unit 7. In an alternative embodiment, the echo ultrasonic signals placed in intermediate storage are subjected to a Hilbert transformation by the transforming unit 7 and absolute value formation.

The data processing unit 4 also comprises time-displacement units 8, 9 which permit in-phase addition of the contributing echo ultrasonic signals. The time-displacement is carried out dependent upon the distance d calculated by the distance calculating unit 5. By means of a summation circuit or adding circuit 10, direction-dependent in-phase addition of the echo ultrasonic signals read out of the data store 3 is undertaken for the different measuring points. The direction-dependent in-phase addition can be carried out, for example, by weighting of a sine or cosine factor for the determined direction. Subsequently, the added-together, weighted signal can be smoothed by a low-pass filter 11 of the data processing unit 4.

The data processing unit 4 also has an analyzing unit 12. The analyzing unit 12 statistically analyzes the angular characteristic of the echo ultrasonic signals dependent upon the sound emission direction. The angular characteristic shows the dependency of the signal amplitude on the sound emission direction. In a possible embodiment, the analyzing unit 12 calculates a possible future failure probability of the respective component B, depending on the determined orientation of the defect present in the component B, based on geometric data of the component B. In one possible embodiment, the analyzing unit 12 has access to a data store 13 in which geometric data of the component B under investigation are stored.

In another possible embodiment, the analyzing unit 12 calculates a future failure probability for the component, based on the determined orientation of the defect present in the component B, using the geometric data of the component read out of the data store 13. Preferably, mechanical loading forces, which can act upon the component B during operation of the component B are taken into account.

For orientation of the defect in the component B, in a possible embodiment, the data processing unit 4 outputs a two-dimensional plane orientation angle. It is also possible for the data processing unit 4 to output a three-dimensional spatial orientation angle of the defect. In another possible embodiment, a color-coded representation of the directional information of in-phase echo totals can be undertaken.

In order to determine the orientation of the defect, a mean value or a median value can be calculated. Furthermore, as a measure for the directional effect of the defect, a standard deviation or a variance can be calculated. The mean value provides an angle, whereas the standard deviation or the variance provides an angular range.

In another possible embodiment, the data processing unit 4 shown in FIG. 1 can be integrated into a machine and can monitor a component B of said machine to determine an orientation of a defect occurring within the component B.

Figure 2:
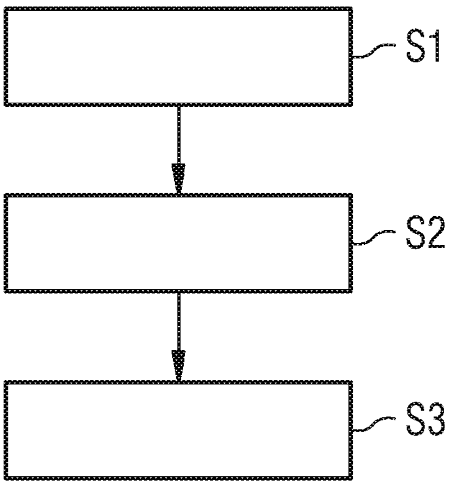
FIG. 2 is a flow diagram of a possible embodiment of a method according to the invention for determining an orientation of a defect present within a mechanical component.

FIG. 2 shows a flow diagram for illustrating the most important steps in the method according to the invention for determining an orientation of a defect present within a mechanical component B.

In a first step S1, initially an ultrasonic signal is applied to the mechanical component B, starting from various measuring points MP. The ultrasonic signals are generated by at least one ultrasonic head 2 which emits ultrasonic signals to the component B at each of the measuring points MP. The ultrasonic head also receives the respective echo ultrasonic signals reflected temporally offset.

In a further step S2, the received echo ultrasonic signals which are reflected by a point P to be investigated within the component B to the measuring points MP are analyzed, depending on a sound emission direction between the respective measuring point MP and the point P to be investigated of the component B, for determining the orientation of a defect.

In a further step S3, a distance d between the measuring point MP and the point P to be investigated is calculated, depending on a detected signal propagation time between the time point of emission of the ultrasonic signal and the time point of reception of the reflected echo ultrasonic signal, for each measuring point. The echo ultrasonic signals of the point P to be investigated which are received temporally offset at the different measuring points MP are added together in phase for evaluation thereof.

In a possible embodiment, the test object or the component is scanned once or multiple times with ultrasonic heads 2 using different sound incidence angles. An area of interest in the component B is defined and an analysis grid is defined which covers the region of interest in the component B. The grid is prepared finely divided so that no defects can be overlooked. At the grid points, not only does in-phase overlaying of the echo ultrasonic signals take place for all the contributing measuring positions, but also a calculation of the orientation of defects in that a direction or orientation between a contributing measuring point MP and the point P to be investigated takes account of the amplitude of the signal contribution. The determination according to the invention of an orientation of a defect present within a mechanical component B can be carried out, in a possible embodiment, parallel to a conventional SAFT analysis. Alternatively, the method according to the invention can be performed subsequently to a conventional SAFT calculation or analysis. In another possible embodiment, the method according to the invention is carried out subsequently to the manufacturing of the component B. In a further possible embodiment of the method according to the invention, the method is performed during operation of the component B in order to monitor said component.

In possible embodiments, by changing the sequence of calculation steps, a calculation time optimization of the data processing unit 4 can be achieved. For example, complex ultrasonic signals can be calculated in advance. In a further possible embodiment, the analysis of the received echo ultrasonic signals is carried out only if the signal amplitude of the in-phase added echo ultrasonic signals exceeds a pre-settable signal threshold value. Furthermore, additional subsequent signal processing, for example, by filtration and smoothing of directional information can be carried out. Furthermore, the SAFT result can be divided or dismantled depending on the determined direction into radial, tangential and axial components.

In one possible embodiment, a vectorial representation of the signal contributions of the various measuring points is carried out. The contribution of the measuring point MP is determined by means of in-phase analysis of the rectified ultrasonic signal. A determination of the vectorial and value sum for characterizing the direction, that is, the direction of the vector sum and the directional effect, that is, the contribution of the vector sum, take place in relation to the absolute value sum. The SAFT result that is determined and the orientation determined can be shown on a display for an operating person with brightness-coding and color-coding. In possible embodiments, a plurality of main directions, i.e. two can be taken into account in the plane or three in space, wherein the main directions can be different in each point P to be investigated. In possible embodiments, the in-phase addition of the ultrasonic signals takes place separately for each main direction. Weighting of the signal contributions with a cosine or sine factor is carried out between the sound propagation direction and the main direction. In possible embodiments, the main directions are perpendicular to one another. In alternative embodiments, the main directions are not perpendicular to one another. The number of main directions can vary. In one possible embodiment, recalculation of the results from different main directions according to quantity and phase is carried out. The calculation results determined with the method according to the invention can be used to feed in the defect positions and defect orientation into a mechanical simulation of the component B under test, for example, in order to evaluate defects found and to calculate a future failure probability. For example, components B which have smaller defects with non-critical orientations can be approved for use or operation, including for higher loading levels. With the method according to the invention, the orientation of a defect is characterized with simultaneously good separation or resolution of closely adjacent defects. With the method according to the invention, the detection sensitivity is increased by reducing noise and the divergence of the ultrasonic signal. The information gathered concerning the defect orientation can be considered in conjunction with the radial, tangential or axial tensions or forces taken into account during design, so that the admissibility of defects can be better evaluated, particularly if a component B is loaded mainly in one particular direction. In this way, manufactured components B can be approved that would otherwise have to be rejected by reason of the safety margin, although such components were per se usable. The components B investigated with the method according to the invention can be approved for operation under greater loading. The method according to the invention can be used in a possible embodiment, including for an immersion testing method. In one possible embodiment, the data processing unit 4 has an input device or an interface by means of which additional information concerning the component A can be specified. For example, one or more material constants of the component material can be input via the interface. It is also possible to input a propagation speed of ultrasonic signals in the component B under investigation via said interface and possibly to store said speed in a suitable data store. In a further possible embodiment, the data processing unit 4 also comprises an interface for the connection of measuring sensors which measure loading forces which act upon the component B during operation thereof. In another possible embodiment, the data store 3 is integrated into the data processing unit 4 and connected via an interface to one or more ultrasonic heads 2. Reception of the ultrasonic time signals and the coordinates of the measuring points MP can take place via a wireless or wire-bound interface with the data processing unit 4. The ultrasonic heads 2 can be connected, for example, via a data network to the data processing unit 4. Furthermore, it is possible that the coordinates of the measuring points MP and the corresponding ultrasonic time signals are locally recorded in a data store 3. Said local data store can be, for example, a portable data carrier. It is also possible that different units of the data processing unit 4 are integrated into a common calculating unit. Thus, for example, the orientation calculating unit 6, the distance calculating unit 5 and the transforming unit 7 can be implemented by means of one or more microprocessors. Furthermore, in another possible embodiment, the movement of the ultrasonic head 2, for example, on the surface of the test object B under investigation can be controlled depending on the measured data. If, for example, an interesting site within the component B is discovered with the ultrasonic head 2, the ultrasonic head 2 can be moved specifically by the data processing unit 4 to suitable measuring points $MP_i$ in order to gather more data for orientation of the detected defect. The defects occurring within the component B are, above all, unwanted defects such as cracks and the like. In one possible embodiment, the defects present in the component B can also be desirable recesses, for example, hollow spaces or bores, so that with the method according to the invention, it is checked whether the orientation and extent of the defect corresponds to the specifications and target values. In other possible embodiments, the frequency at which the ultrasonic signal is emitted from the ultrasonic head 2 into the component B under investigation is adjustable. In this way, it is possible to investigate different sites and/or defects with different sound frequencies.

We claim:

1. A method for determining an orientation of a defect present within a mechanical component, comprising:

applying ultrasonic signals emitted from various measuring points to the mechanical component, wherein the ultrasonic signals are generated by at least one ultrasonic head which applies an ultrasonic signal to the component at each of the measuring points, wherein an echo ultrasonic signal thereby generated is received temporally offset by said ultrasonic head or a different ultrasonic head in each case; and calculating an angular characteristic of the received echo ultrasonic signals depending on a sound emission direction between the respective measuring point and the point to be investigated, wherein the angular characteristic gives a dependency of the signal amplitude on the sound emission direction, wherein, depending on a detected signal propagation time between the time point of emission of the ultrasonic signal and the time point of reception of the reflected echo ultrasonic signal for each measuring point, a distance between the measuring point and the points under investigation is calculated and the echo ultrasonic signals from the points under investigation and received temporally offset at the different measuring points are added together in phase for the analysis thereof, and wherein the phase characteristic is analyzed to statistically determine the orientation of the defect.

2. The method as claimed in claim 1, wherein the echo ultrasonic signals received temporally offset at the different measuring points are added together in phase taking account of an angular characteristic of the ultrasonic head.

3. The method as claimed in claim 2, wherein an envelope curve is determined for the echo ultrasonic signals placed in intermediate storage.

4. The method as claimed in claim 3, wherein the echo ultrasonic signals placed in intermediate storage are rectified and low-pass filtered.

5. The method as claimed in claim 3, wherein the echo ultrasonic signals placed in intermediate storage are subjected to a Hilbert transformation and absolute value generation.

6. The method as claimed in claim 1, wherein, in order to determine the orientation of the defect, a mean value or a median value is calculated.

7. The method as claimed in claim 1, wherein a measure for the directional effect of the defect, in particular a standard deviation, is calculated.

8. The method as claimed in claim 1, wherein the different echo ultrasonic signals that are received at the different measuring points by the ultrasonic head are placed in intermediate storage in a memory store together with the spatial coordinates of the respective measuring point.

9. The method as claimed in claim 1, wherein analysis of the echo ultrasonic signals received takes place only once the signal amplitude of the in-phase added-together echo ultrasonic signals exceeds a settable threshold value.

10. The method as claimed in claim 1, wherein a direction-dependent in-phase addition of the echo ultrasonic signals is carried out.

11. The method as claimed in claim 1, wherein as the orientation of the defect, a two-dimensional plane orientation angle or a three-dimensional solid orientation angle of the defect is output.

12. The method as claimed in one of claim 1, wherein, depending on the determined orientation of the defect present in the component and based on stored geometric data of the component, a future failure probability of the component is calculated.

13. The method as claimed in claim 12, wherein in order to calculate the failure probability of the component, mechanical loading forces which act upon the component during operation are taken into account.

14. The method as claimed in claim 1, wherein during evaluation of an indication, the orientation as determined is taken into account in order to detect a correct indication variable.

15. A device for determining an orientation of a defect present within a mechanical component, comprising:

at least one ultrasonic head which applies ultrasonic signals to the mechanical component from various measuring points, wherein echo ultrasonic signals which are reflected by points to be investigated present within the component to the measuring points, are received by the same or another ultrasonic head;

a data processing unit which is configured to calculate an angular characteristic of the received echo ultrasonic signals depending on a sound emission direction between the respective measuring point and the points to be investigated, wherein the angular characteristic gives a dependency of the signal amplitude on the sound emission direction, wherein the data processing unit is configured, depending on a detected signal propagation time between the time point of emission of the ultrasonic signal and the time point of reception of the echo ultrasonic signal reflected by a defect for each measuring point, to calculate a distance between the measuring point and the points to be investigated, and to add together in phase the echo ultrasonic signals of the points to be investigated received temporally offset at the various measuring points for the analysis thereof; and an analysis unit, which is configured to statistically analyze the angular characteristic to determine the orientation of a defect.

16. The device as claimed in claim 15, wherein an ultrasonic head is provided which is movably arranged on the surface of the mechanical component and is configured to generate the ultrasonic signals and to apply ultrasonic signals to the mechanical component from the measuring points.

17. The device as claimed in claim 16, wherein an array test head is provided which is configured to generate the ultrasonic signals with a plurality of ultrasonic heads.

18. The device as claimed in claim 15, comprising a memory store which places the various echo ultrasonic signals that are received at the different measuring points together with the spatial coordinates of each measuring point into storage for further analysis.

19. The device as claimed in claim 18, wherein a transforming unit is provided which is configured to subject the echo ultrasonic signals placed in intermediate storage in the memory store to a Hilbert transformation and absolute value formation.

20. The device as claimed in claim 18, wherein a transforming unit is provided which is configured to rectify and deep-pass filter the echo ultrasonic signals placed in intermediate storage in the memory store.

21. The device as claimed in claim 15, wherein the analyzing unit is configured to calculate a future failure probability for the component depending on the orientation of the defect present in the component as determined and based on stored geometric data of the component.

22. A machine, comprising:

a device as claimed in claim 15, wherein the device monitors a component of the machine in order to determine an orientation of a defect occurring within the component.

* * * * *